United States Patent [19]

Yamamoto et al.

[11] 4,202,974
[45] May 13, 1980

[54] PROCESS FOR PREPARING 3,4-DIHYDRO-2(1H)-QUINAZOLINONE DERIVATIVES

[75] Inventors: Michihiro Yamamoto, Nishinomiya; Shigenari Katayama, Takarazauka; Masao Koshiba, Nishinomiya; Hisao Yamamoto, Kobe, all of Japan

[73] Assignee: Sumitomo Chemical Company, Limited, Osaka, Japan

[21] Appl. No.: 731,574

[22] Filed: Oct. 12, 1976

[30] Foreign Application Priority Data

Oct. 24, 1975 [JP] Japan .................................. 50-128578

[51] Int. Cl.² .................. A61K 31/505; C07D 239/82; C07D 491/04
[52] U.S. Cl. .................................... 544/251; 544/284; 544/286
[58] Field of Search ................. 260/251 QB; 544/251, 544/284, 286

[56] References Cited

U.S. PATENT DOCUMENTS

| | | | |
|---|---|---|---|
| 3,686,178 | 8/1972 | Cooke et al. | 260/251 QB |
| 3,748,331 | 7/1973 | Cooke et al. | 260/251 QB |
| 3,764,600 | 10/1973 | Ott | 260/251 QB |
| 3,829,420 | 8/1974 | Inaba et al. | 260/251 QB |

*Primary Examiner*—Donald G. Daus
*Assistant Examiner*—James H. Turnipseed
*Attorney, Agent, or Firm*—Stevens, Davis, Miller & Mosher

[57] ABSTRACT

3,4-Dihydro-2(1H)-quinazolinones and quniazolinethiones such as 1-cyclopropylmethyl-4-phenyl-6-methoxy-3,4-dihydro-2(1H)-quinazolinone and its thione derivative, are prepared in high yield with high purity by heating the corresponding arylurea or thiourea such as N-cyclopropylmethyl-N-(p-methoxyphenyl) urea or its thiourea derivative, with the corresponding aldehyde such as benzaldehyde in the presence of hydrobromic acid in an inert solvent.

2 Claims, No Drawings

PROCESS FOR PREPARING 3,4-DIHYDRO-2(1H)-QUINAZOLINONE DERIVATIVES

The present invention relates to a novel process for preparing 3,4-dihydro-2(1H)-quinazolinone derivatives.

There has heretofore been proposed to prepare 3,4-dihydro-2(1H)-quinazolinone derivatives by reacting a corresponding arylurea or thiourea with a corresponding aldehyde, as described in U.S. Pat. Nos. 3,748,331 and 3,829,420. These patents disclose that the use of arylsulfonic acids, alkylsulfonic acids, trifluoroacetic acid and hydrogen chloride as catalyst is suitable and that the reaction is effectively carried out under anhydrous conditions. According to these prior processes, however, even when methanesulfonic acid, which is described as a preferred catalyst from among the known acids, is used, the yield of the desired 3,4-dihydro-2(1H)-quinazolinones is about 65% at best. Moreover many by-products are formed when the corresponding urea are used as a starting material. Furthermore, 3,4-dihydro-2(1H)-quinazolinethiones are only obtained in an extremely low yield or can hardly be obtained by the reaction of the corresponding thiourea with the aldehyde under the known reaction conditions.

In order to solve such problems of the prior processes, we have extensively studied the conditions of this reaction and surprisingly found that, when the reaction is carried out by using hydrobromic acid (aqueous hydrogen bromide solution) as catalyst, the desired 3,4-dihydro-2(1H)-quinazolinone derivatives are obtained in much higher yield with high purity in case of both quinazolinones and quinazolinethiones.

The present invention provides a novel process for producing a 3,4-dihydro-2(1H)-quinazolinone derivative of the formula,

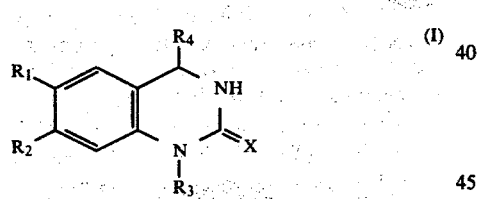

wherein $R_1$ and $R_2$ are each hydrogen, lower alkyl, lower alkylthio or lower alkoxy, or, when taken together, $R_1$ and $R_2$ may form methylenedioxy; $R_3$ is lower alkyl or lower cycloalkylalkyl; $R_4$ is phenyl, halophenyl, lower alkoxyphenyl, lower alkylphenyl or thienyl; and X is oxygen or sulfur, which comprises reacting a compound of the formula,

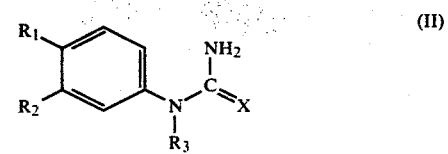

wherein $R_1$, $R_2$, $R_3$ and X are as defined above, with a compound of the formula, $$R_4—CHO \quad (III)$$

wherein $R_4$ is as defined above, with heating in the presence of hydrobromic acid in an inert solvent.

In the present specification, the term "lower alkyl" is intended to mean alkyl having 1 to 4 carbon atoms, e.g. methyl, ethyl, n-propyl, isopropyl, n-butyl or isobutyl; and the term "lower alkoxy" may means $C_{1-4}$ alkoxy, e.g. methoxy, ethoxy, n-propoxy, isopropoxy, n-butoxy or isobutoxy; the term "cycloalkylalkyl" may mean $C_{3-6}$ cycloalkyl $C_{1-4}$ alkyl, e.g. cyclopropylmethyl, cyclopropylethyl, cyclobutylmethyl, cyclopentylmethyl or cyclohexylmethyl; and the term "halophenyl" may mean o-fluorophenyl, p-fluorophenyl, o-chlorophenyl, m-chlorophenyl or p-chlorophenyl.

In carrying out the process of the present invention, the amount of hydrobromic acid used is preferably in the range of 1.0 to 0.01 molar equivalent based on the compound of the formula (II). The hydrobromic acid which may be conveniently used is ordinary concentrated aqueous hydrogen bromide solution. The reaction is effectively carried out by heating under reflux in an inert solvent using a water separator. The suitable solvent may be benzene, toluene, xylene, chlorobenzene, dichloroethane, tetrachloroethane or the like. In general, the reaction is effected by employing a substantially equimolar mixture of the reactants (II) and (III). Accordingly to the process of the present invention the reaction can be completed within about 10 hours.

The quinazolinone derivatives of the formula (I) which are obtained in accordance with the process of the present invention, have anti-inflammatory and analgesic activities by themselves. Further, they are also very useful as starting materials for the synthesis of the compounds of the formula,

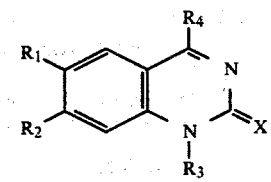

wherein $R_1$, $R_2$, $R_3$, $R_4$ and X are as defined above, which are excellent anti-inflammatory and analgesic agents.

The present invention will be illustrated in more detail with reference to the following examples, which are only illustrative, but do not limit the scope of the present invention.

EXAMPLE 1

To a suspension of 28.6 g (0.13 mole) of N-cyclopropylmethyl-N-(p-methoxyphenyl) urea in 140 g of toluene were added 13.8 g (0.13 mole) of benzaldehyde and 0.55 g (0.0033 mole) of a 48% hydrobromic acid. The resulting mixture was heated under relux for 10 hours with stirring using a water separator. Thereafter the solvent was removed under reduced pressure and the residue was suspended in a mixture of 80 ml of methanol and 40 g of a 2% hydrochloric acid. The mixture was cooled with ice with stirring. The precipitated crystals were collected by filtration, washed with a mixture of methanol-2% hydrochloric acid (2:1) and then with water, and dried to give 32.0 g (80%) of 1-cyclopropylmethyl-4-phenyl-6-methoxy-3,4-dihydro-2(1H)-quinazolinone, m.p. 133° C.

EXAMPLE 2

According to the procedure similar to that described in Example 1, the following compounds were obtained in high yield from the corresponding N-substituted-N-arylureas and aldehydes.

1-Cyclopropylmethyl-4-phenyl-7-methoxy-3,4-dihydro-2(1H)-quinazolinone   m.p. 135°–137° C.

1-Cyclopropylmethyl-4-phenyl-6-methyl-3,4-dihydro-2(1H)-quinazolinone   m.p. 131°–132° C.

1-Cyclopropylmethyl-4-phenyl-7-methyl-3,4-dihydro-2(1H)-quinazolinone   m.p. 138°–139° C.

1-Cyclopropylmethyl-4-phenyl-6-methylthio-3,4-dihydro-2(1H)-quinazolinone   m.p. 159°–160° C.

1-Cyclopropylmethyl-4-phenyl-6,7-methylenedioxy-3,4-dihydro-2(1H)-quinazolinone   m.p. 175°–176° C.

1-Cyclopropylmethyl-4-(o-fluorophenyl)-6-methoxy-3,4-dihydro-2(1H)-quinazolinone   m.p. 133°–135° C.

1-Cyclopropylmethyl-4-(p-fluorophenyl)-6-methoxy-3,4-dihydro-2(1H)-quinazolinone   m.p. 164°–166° C.

1-Cyclopropylmethyl-4-(p-chlorophenyl)-6-methoxy-3,4-dihydro-2(1H)-quinazolinone   m.p. 147°–149° C.

1-Cyclopropylmethyl-4-(o-tolyl)-6-methoxy-3,4-dihydro-2(1H)-quinazolinone   m.p. 124°–126° C.

1-Cyclopropylmethyl-4-(p-methoxyphenyl)-6-methoxy-3,4-dihydro-2(1H)-quinazolinone   m.p. 146°–148° C.

1-Cyclopropylmethyl-4-(2-thienyl)-6-methoxy-3,4-dihydro-2(1H)-quinazolinone   m.p. 145°–146° C.

1-Cyclopropylmethyl-4-(2-thienyl)-6-methylthio-3,4-dihydro-2(1H)-quianzolinone   m.p. 143°–144° C.

1-Ethyl-4-phenyl-6-methoxy-3,4-dihydro-2(1H)-quianzolinone   m.p. 153°–153.5° C.

1-Isopropyl-4-phenyl-6-methoxy-3,4-dihydro-2(1H)-quinazolinone   m.p. 149°–150° C.

1-Isopropyl-4-phenyl-7-methyl-3,4-dihydro-2(1H)-quinazolinone   m.p. 160° C.

1-Isopropyl-4-phenyl-6,7-methylenedioxy-3,4-dihydro-2(1H)-quinazolinone   m.p. 168°–170° C.

EXAMPLE 3

To a suspension of 2.36 g (0.01 mole) of N-cyclopropylmethyl-N-(p-methoxyphenyl) thiourea in 30 ml of toluene were added 1.21 g (0.011 mole) of benzaldehyde and 0.84 g (0.005 mole) of 48% hydrobromic acid. The resulting mixture was heated under reflux for 6 hours using a water separator. After cooling, the reaction mixture was washed with dilute hydrochloric acid and then with water, and dried over anhydrous sodium sulfate. The solvent was removed under reduced pressure and the residue was recrystallized from isopropyl alcohol to give 2.33 g (72%) of 1-cyclopropylmethyl-4-phenyl-6-methoxy-3,4-dihydro-2(1H)-quinazolinethione, m.p. 146°–147° C.

What is claimed is:

1. A process for preparing a 3,4-dihydro-2(1H)-quinazolinone derivative of the formula,

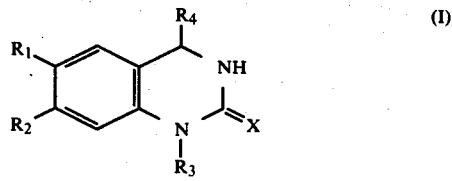

wherein $R_1$ and $R_2$ are each hydrogen, lower alkyl, lower alkylthio or lower alkoxy, or, when taken together, $R_1$ and $R_2$ may form methylenedioxy; $R_3$ is lower alkyl or lower cycloalkylalkyl; $R_4$ is phenyl, halophenyl, lower alkoxyphenyl, lower alkylphenyl or thienyl; and X is oxygen or sulfur, which comprises reacting a compound of the formula,

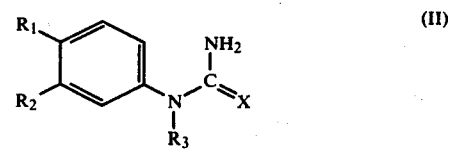

wherein $R_1$, $R_2$, $R_3$ and X are as defined above, with a compound of the formula,

$$R_4\text{—CHO} \qquad (III)$$

wherein $R_4$ is as defined above, with heating under reflux in an inert solvent selected from the group consisting of benzene, toluene, xylene, chlorobenzene, dichloroethane and tetrachloroethane in the presence of hydrobromic acid, which is used in an amount of 1.0 to 0.01 molar equivalent based on the compound of formula (II).

2. A process according to claim 1, wherein the reaction is carried out in toluene at the reflux temperature of the reaction mixture.

* * * * *